(12) United States Patent
Hafner et al.

(10) Patent No.: US 10,238,569 B2
(45) Date of Patent: Mar. 26, 2019

(54) FASTENING UNIT FOR FASTENING A DEVICE FOR SUPPORTING A PATIENT TO BE X-RAYED TO AN OPERATING TABLE

(71) Applicant: MAQUET GMBH, Rastatt (DE)

(72) Inventors: Dieter Hafner, Offenburg (DE); Siegfried Hund, Oberkirch (DE); Ulrich Wyslucha, Weingarten (DE)

(73) Assignee: MAQUET GMBH, Rastatt (DE)

( * ) Notice: Subject to any disclaimer, the term of this patent is extended or adjusted under 35 U.S.C. 154(b) by 542 days.

(21) Appl. No.: 15/085,676

(22) Filed: Mar. 30, 2016

(65) Prior Publication Data

US 2016/0213543 A1    Jul. 28, 2016

Related U.S. Application Data

(63) Continuation-in-part of application No. PCT/EP2014/072322, filed on Oct. 17, 2014.

(30) Foreign Application Priority Data

Oct. 18, 2013  (DE) .................. 10 2013 111 522

(51) Int. Cl.
*A61B 6/04* (2006.01)
*A61G 13/10* (2006.01)
*A61G 13/12* (2006.01)

(52) U.S. Cl.
CPC ........ *A61G 13/1205* (2013.01); *A61B 6/0407* (2013.01); *A61G 13/101* (2013.01);
(Continued)

(58) Field of Classification Search
CPC .............. A61G 13/1205; A61G 13/128; A61G 13/101; A61G 13/1225; A61G 13/122; A61G 13/1285; A61B 6/0407
See application file for complete search history.

(56) References Cited

U.S. PATENT DOCUMENTS 3,622,021 A * 11/1971 Heath .................... B65G 67/00
414/361
4,018,412 A * 4/1977 Kees, Jr. .............. A61G 13/101
24/486
(Continued)

FOREIGN PATENT DOCUMENTS

CN         1828071 A     9/2006
CN       201397962 Y     2/2010
(Continued)

OTHER PUBLICATIONS

International Search Report dated Feb. 4, 2015 issued for corresponding international application No. PCT/EP2014/072322, 6 pages, with translation.
(Continued)

*Primary Examiner* — Robert G Santos
*Assistant Examiner* — Myles A Throop
(74) *Attorney, Agent, or Firm* — Aaron M. Miller

(57) ABSTRACT

A fastening device is disclosed. The fastening device has a housing having a receptacle that receives a coupler of an operating table device and a locking member connected to the housing and movable relative to the housing between a locked position and an unlocked position. The locking member retains the coupler in the receptacle in the locked position, and the locking member releases the coupler from the receptacle in the unlocked position. The fastening device also has a resilient member that urges the locking member toward the locked position, an actuation member that moves the locking member from the locked position to the unlocked position, and a ratchet assembly that maintains the locking member in the unlocked position.

20 Claims, 9 Drawing Sheets

(52) U.S. Cl.
CPC ......... *A61G 13/122* (2013.01); *A61G 13/128* (2013.01); *A61G 13/1225* (2013.01); *A61G 13/1285* (2013.01)

(56) References Cited

U.S. PATENT DOCUMENTS

| | | | |
|---|---|---|---|
| 5,088,706 A | 2/1992 | Jackson | |
| 5,147,287 A | 9/1992 | Jewell et al. | |
| 5,806,117 A | 9/1998 | Goffried | |
| 5,908,053 A * | 6/1999 | Byrd | B01D 53/0446 137/614.06 |
| 6,076,525 A | 6/2000 | Hoffman | |
| 6,154,901 A | 12/2000 | Carr | |
| 7,520,007 B2 | 4/2009 | Skripps | |
| 7,520,008 B2 | 4/2009 | Wong et al. | |
| 7,600,281 B2 | 10/2009 | Skripps | |
| 7,896,569 B2 * | 3/2011 | Katzenstein | A61G 13/12 403/101 |
| 9,161,875 B2 * | 10/2015 | Clark | A61G 13/0036 |
| 2005/0081865 A1 | 4/2005 | Hubert et al. | |
| 2006/0242765 A1 | 11/2006 | Skripps et al. | |
| 2006/0248650 A1 | 11/2006 | Skripps | |
| 2006/0255220 A1 | 11/2006 | Skripps | |
| 2006/0284468 A1 | 12/2006 | Tanaka | |
| 2009/0283657 A1 * | 11/2009 | Silvers | A47G 1/205 248/550 |
| 2011/0113558 A1 | 5/2011 | Olszewski et al. | |

FOREIGN PATENT DOCUMENTS

| | | |
|---|---|---|
| CN | 101689729 A | 3/2010 |
| DE | 102006059733 A1 | 6/2008 |
| DE | 102009004554 A1 | 7/2009 |
| DE | 202013100213 U1 | 3/2013 |
| EP | 1785123 A2 | 5/2007 |
| EP | 2325502 A1 | 5/2011 |
| RU | 2161942 C1 | 1/2001 |
| WO | 2009/029524 A1 | 3/2009 |
| WO | 2013/069952 A1 | 5/2013 |
| WO | 2014/057344 A2 | 4/2014 |

OTHER PUBLICATIONS

Russian Search Report dated Apr. 6, 2018, which issued during the prosecution of corresponding Russian Patent Application No. 2016118588, 3 pages.

Chinese Office Action and Chinese Search Report (with English translation) dated Feb. 28, 2017, which issued during the prosecution of corresponding Chinese Patent Application No. 201480065232.3, 19 pages.

* cited by examiner

FASTENING UNIT FOR FASTENING A DEVICE FOR SUPPORTING A PATIENT TO BE X-RAYED TO AN OPERATING TABLE

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2014/072322, filed Oct. 17, 2014, and which designates the United States of America, and German Patent Application No. 10 2013 111 522.5, filed Oct. 18, 2013. The disclosures of these applications are herein incorporated by reference in their entirety.

TECHNICAL FIELD

The present disclosure relates to an operating-table-side fastening unit for fastening a device (e.g., for supporting a patient who is to be x-rayed) to an operating table, which may comprise a base body which has a receptacle for receiving a coupling element of a device-side fastening unit fastenable to the device. On a base body a locking bar may be fastened movably relative to said base body, wherein, in a locked position, the locking bar may substantially prevent the coupling element from being removed from the receptacle, and, in an unlocked position, the locking bar may allow the coupling element to be removed from the receptacle. Furthermore, the present disclosure relates to a device-side fastening unit for fastening a device for supporting a patient, who is to be x-rayed, to an operating table, which may comprise an intermediate piece which has a coupling element for introduction into a receptacle of the operating-table-side fastening unit. In addition, the present disclosure relates to an arrangement which comprises an operating table, a device for supporting a patient who is to be x-rayed, as well as operating-table-side and device-side fastening units for fastening the device to the operating table.

BACKGROUND

In various operations, for example in back surgery, a patient is typically x-rayed during the operation. For this purpose, C-shaped x-ray apparatuses are commonly used, wherein the patient is supported in the opening of the "C." For example, C-arcs that can be swiveled by up to 270° are also used for recording 3D images. The use of conventional operating tables for supporting the patient is typically not suitable for this purpose, because x-raying is practical in a limited range. For recording 3D-views, it is appropriate to move the C-arc relatively closely to the patient over a relatively large area. The standard patient rests of operating tables are typically configured too wide to be suitable for this purpose. On the other hand, the operating table frequently comprises thick, metal-containing constructions, so that x-raying occurs with unsuitable results. Another factor that adds to the challenge for x-raying is that the thicknesses and the contours of the constructions are different, which may not be suitable for x-ray imaging or x-ray recording using the C-arc.

Therefore, devices typically used for supporting the patient are attached to the operating table. The patient's torso, which is to undergo the surgery and is to be x-rayed, then rests on the attached device and the legs of the patient rest on the operating table itself.

Such a device for supporting a patient during surgery is known, for example, from the document U.S. Pat. No. 7,600,281 B2. The device described therein comprises two bars extending parallel to one another that are fastened on one side to the operating table and on the other side to a stand. On the bars, several resting surfaces are provided, on which the patient, for example the torso and hips of the patient, can be supported. Here, the resting surfaces protrude over substantially the entire area between the two bars, connecting them to one another.

The above-described device has the disadvantage that, due to the resting elements, the quality of a recorded x-ray image can be unsuitable. The contours of the resting elements may enter into the x-ray image, which may be unsuitable for the use of the image. In addition, the rigid resting elements may not allow for adaptation to the individual contours of the patient, so that the patient can possibly not be suitably supported for the operation.

In conventional devices, the rails may be fastened to the operating table via the two interfaces, wherein, between the two interfaces, a cross connection exists, in that an operating element is provided, so that the two interfaces can be unlocked with the aid of an operating element, and so that the device can be released from the operating table. In addition, as a frame, an additional metal cross connection can be provided. This has the disadvantage, on the one hand, that the permeability to x-rays is not suitable in this area, which can lead to unsuitable x-ray images, and, on the other hand, that the available adjustment range for the operating table and the patient-supporting units relative to one another is unsuitable. For example, a height adjustment between the rails and the operating table may be unsuitable, and an angling of the fastening arrangements relative to the operating table may not exceed approximately 50°, which may be unsuitable.

SUMMARY OF THE DISCLOSURE

An exemplary operating-table-side fastening unit for fastening a rail of a device for supporting a patient to be x-rayed to an operating table is disclosed. An exemplary device-side fastening unit for fastening a device for supporting a patient to be x-rayed to an operating table, and an arrangement consisting of an operating table are also disclosed.

An exemplary device for supporting a patient to be x-rayed, and fastening units, are also disclosed. The above exemplary disclosed assemblies may be easy to operate, allow a secure fastening, may allow suitable possibilities for adjustment, and may allow for the recording of high-value x-ray images of suitable quality in a relatively large area.

A resilient element may be provided, which preloads the locking bar in the locking position. By using an actuation element for manually moving the locking bar, the locking bar can be moved against the resilient force of the preloading element from the locked position into the unlocked position. Furthermore, the operating-table-side fastening unit may comprise a ratchet mechanism for holding the locking bar in the unlocked position, wherein this ratchet mechanism may hold the locking bar in the unlocked position, when a coupling element is arranged in the receptacle and the locking bar has been moved via the actuation element in the unlocked position or past this unlocked position (e.g., at least until the coupling element has been removed from the receptacle or the actuation element has been actuated again).

Accordingly, both for the release of the device-side attachment unit and also for the removal of the coupling element from the receptacle, the actuation element may be actuated (e.g., only) once, and subsequently the locking bar may be held in the unlocked position, so that an operator has both hands free to unfasten the device. In particular, in the case in which two operating-table-side fastening elements are used on two rails extending parallel to one another, or in another embodiment with two interfaces for the fastening to the operating table, they can thus be released conveniently one after the other. Due to the automatic release of the ratchet mechanism, e.g., due to the fact that the ratchet mechanism may no longer hold the locking bar in the unlocked position when the coupling element has been removed from the receptacle, it is achieved that the locking bar is automatically arranged again in the locking position and thus, when a new coupling element is fed into the receptacle, it is automatically arranged in the locked position and suitably holds the coupling element in this locked position.

Alternatively, the ratchet mechanism can also be released via a renewed actuation of the actuation element, which may have the advantage that, in the case of inadvertent actuation of the actuation element, the locked position can be reestablished without having to remove the coupling element from the receptacle for this purpose. Hereby, user comfort may be increased.

The actuation of the actuation element may include the actuation element being actuated (e.g., completely actuated) up to an abutment.

The ratchet mechanism may be configured, for example, as a flip-flop mechanism. Alternatively, the ratchet mechanism can also be implemented, for example, by using a guide cam.

The device for supporting may comprise, for example, two rails which can be fastened in each case via an operating-table-side fastening unit and via a device-side fastening unit to the operating table. The device-side fastening unit may be, for example, a rail-side fastening unit.

Alternatively, the device can also comprise (e.g., only) one rail with side arms or more than two rails, such as for example, three or four rails. Furthermore, alternatively, a structure formed in one piece, in particular from carbon-fiber-reinforced plastic, can be used.

The coupling element may be configured, for example, as a rod. Alternatively, a ball, a ring guided over a hook, or any other form that allows a tilting of the device for supporting the patient relatively to the OP table may be used.

For example, the resilient element may be a torsion spring, the first end of which may be supported on the base body and the second end of which may be supported on the locking bar.

In particular, the locking bar may be guided in the base body in such a manner that the locking bar moves on a circular track or an approximately circular track (e.g., an elliptical track or substantially circular track), and therefore the locking bar may be a rotation locking bar (e.g., configured in the shape of an arc and adapted to the guide track thereof).

The receptacle may be configured in the shape of a "V," whereby a substantially secure holding of the coupling element of the device-side fastening element in the receptacle may be achieved. The bottom area of the receptacle (e.g., the area that faces the opening of the "V") may be rounded, and may be configured to be complementary to the coupling element. Thus, the play between the receptacle and the coupling element may be minimized, so that a substantially secure supporting is provided.

The actuation element may comprise a pull lever fastened to the locking bar, which may be configured and mounted so that it can be used both for moving the locking bar from the locked position into the unlocked position and also for releasing the ratchet mechanism (e.g., so that as the coupling element is received, the locking bar may be moved by resilient elements back into the locked position, from which the base body may be pulled back). Hereby it may be achieved that the pull lever is actuated in a substantially similar way, independently of whether the locking bar is to be moved from the locked position into the unlocked position, or from the unlocked position into the locked position. For example, in the case in which the fastening element is aligned in accordance with its intended purpose, the pull lever is arranged on the lower side of the fastening unit, so that it cannot as easily be actuated inadvertently and so that it does not act as an obstacle (e.g., hang around in the way). For example, the pull lever may be rotatably arranged on the locking bar, so that it can be folded back in a space-saving manner.

In at least some exemplary embodiments, a gravity pendulum may be rotatably fastened to the locking bar, and, based on the gravitational force thereof, the gravity pendulum maintains alignment thereof in space (e.g., a substantially absolute alignment), independently of the alignment of the fastening unit. The gravity pendulum may be configured so that it substantially prevents an actuation of the actuation element when an actuation unit is arranged outside of a predetermined alignment range relative to the horizontal. The operating-table-side fastening unit may be received, for example, in receptacles of the operating table, wherein these may be configured so that the operating-table-side fastening unit can be tilted both upward and also downward relative to the horizontal. Hereby, a suitable adjustability (e.g., a relatively large adjustability) may be achieved, in that, via this adjustability, the angle between the device and the operating table can be set.

By the provision of a gravity pendulum, a releasing of the locking may occur (e.g., only occur) when the operation-side fastening unit is arranged approximately horizontally, so that, in particular, a release may be substantially prevented when the fastening unit is inclined (e.g., when inclined so far that, due to the gravitational force thereof, and without the locking bar of the coupling element, it may slip automatically out of the receptacle).

Furthermore, for example, if the end of the locking bar that protrudes into the receptacle, to the extent that it is arranged in the locked position, prevents a removal of the coupling element from the receptacle, it may be beveled in such a manner that the locking bar, as the coupling element is introduced in the receptacle, is moved automatically out of the locked position (e.g., due to the contact with the coupling element, so that the coupling element can be introduced into the receptacle). For example, the locking bar may not be moved sufficiently far in the direction of the unlocked position so that it is arranged completely in the unlocked position (e.g., it may not be moved sufficiently far for the ratchet mechanism to be able to hold the locking bar firmly depending on the position of the ratchet mechanism). In this manner, one may achieve simple handling, because the coupling element may simply be pressed into the receptacle, without actuation of the locking bar for this purpose. On the other hand, the locking bar again may move automatically into the locked position, so that suitable operation is achieved. Thus, in particular, the ratchet mechanism may be prevented from inadvertently holding the locking bar fixed in the unlocked position.

In an exemplary embodiment, the fastening unit may comprise a feeler rotatably fastened to the base body for detecting the reception of a coupling element in the receptacle, which may be preloaded via another resilient element in a first position in which it protrudes at least partially into the receptacle. In a second position, the feeler may be moved relative to the first position against the resetting force of the additional resilient element (e.g., out of the receptacle into the base body). The feeler may be configured so that, as the coupling element is introduced into the receptacle, it is automatically moved from the first position into the second position and held by the received coupling element in this second position until the coupling element is arranged in the receptacle. For example, by using the feeler, it is possible to determine mechanically (e.g., at substantially any time) whether the coupling element is received in the receptacle. In this way, in particular, as will be explained further below, the automatic release of the ratchet mechanism can take place as the coupling element is removed from the receptacle.

In addition, due to the movement of the feeler from the first position into the second position, an additional resilient element may be moved from the base body in the direction in which the operating table is arranged, by which the play between the fastening unit and the operating table may be reduced (e.g., minimized or substantially eliminated), so that a wobble-free fastening to the operating table may occur. This additional resilient element may be, for example, a silicone block.

For example, the ratchet mechanism may comprise a first ratchet wheel, a second ratchet wheel, and a square washer, which in each case may be mounted in a torsion-proof manner on a common shaft. Furthermore, the ratchet mechanism may have a blocking element which may be preloaded in a blocking position, for example by a spring. In this blocking position, the blocking element may be engaged with the second ratchet wheel and thus may prevent a rotation of the second ratchet wheel in a first direction and therefore also a rotation of the shaft and the elements attached thereto in the first direction. Also for example, if the blocking element is arranged in the released position against the preloading, then a rotation of the shaft in the first direction may be facilitated.

The first ratchet wheel and the second ratchet wheel may be configured, for example, in such a manner that they allow in each case a rotation against the first direction, independently of the position of the blocking element.

For example, the feeler (e.g., to the extent that it is arranged in the first position) may come in contact with the blocking element and, via this contact, may hold this blocking element in the released position against the preloading thereof. Alternatively for example, if the feeler is arranged in the second position, then the feeler may no longer hold the blocking element in the released position, so that the blocking element, due to the preloading thereof, may be moved into the blocking position, and may prevent a rotation of the shaft in the first direction. Using this mechanism, a rotation of the shaft in the first direction may be provided (e.g., only) when the feeler is arranged in the first position (e.g., when no coupling element is arranged in the receptacle). Further for example, if a coupling element is arranged in the receptacle, a rotation of the shaft in the first direction may not occur.

For example, the locking bar may have a protrusion, wherein the protrusion may be engaged with the square washer, when the square washer is aligned in a blocking angular position. The blocking element may be arranged in the blocking position and when the locking bar has been moved by the actuation element (e.g., past the unlocked position), the square washer may hold the locking bar in the unlocked position.

When a coupling element is introduced into the receptacle, the blocking element may be arranged in its blocking position and thus may prevent a rotation of the shaft in the first direction. After the introduction of the coupling element, the locking bar may be arranged automatically in the locked position. If the actuation element is actuated for the unlocking, outward movement may occur (e.g., when the locking bar is actuated first past the unlocked position in which it can be held via the square washer of the ratchet mechanism). To the extent that the square washer may be arranged in a blocking angular position, the protrusion may engage with the square washer when the locking bar moves back. For example, the shaft may be rotated against the first direction, so that the square washer may be able to rotate out of the blocking angular position, and for the resilient element of the locking bar element to be able to move this locking bar element from the unlocked position into the locked position. For example, this rotation in the first direction may be prevented by the blocking element being arranged in the blocking position, so that the ratchet mechanism may hold the locking bar in the unlocked position. If the coupling element is removed from the receptacle, the feeler may move into the first position, as a result of which the blocking element may be moved into the released position (e.g., so that the shaft can be rotated in the first direction, which also may occur due to the force exerted by the resilient element of the locking bar). Thus, the ratchet mechanism may automatically be released during the removal of the coupling element, and the locking bar may be moved from the unlocked position into the locked position.

Alternatively, for example, if the square washer is arranged in an unblocking angular position, it may allow a movement of the locking bar from the unlocked position into the locked position (e.g., regardless of whether or not the blocking element prevents a rotation of the shaft in the first direction). The shape of the first ratchet wheel and the shape the square washer may be, for example, adapted to one another so that (e.g., during a rotation of the first ratchet wheel by one notch against the first rotation direction) the alignment of the square washer switches respectively between the blocking angular position and the unblocking angular position. For example, the shaft and the square washer may be moved in the same direction, e.g. against the first direction.

The first ratchet wheel may have, for example, more notches than the number of corners on the square washer (e.g., the first ratchet wheel may have twice the number of notches as the number of corners of the square washer). For example, the first ratchet wheel may have eight notches.

For example, on the locking bar, a contact element for contacting the first ratchet wheel may be provided. For example, when the actuation element is actuated, the contact element in each case may contact the first ratchet wheel and, via this contact, may rotate by one notch against the first direction. Thus, with each actuation, the square washer may be varied between the blocking angular position and the unblocking angular position. For example, when the locking bar is moved by a first actuation of the actuation element into the unlocked position, as the coupling element is received in the receptacle, the locking bar can be moved again into the locked position by actuating the actuating element anew.

The contact element may be resiliently mounted relative to the locking bar, wherein, for example, it may be arranged in a recess of the locking bar, and may be movable (e.g., movable sufficiently far so that it can be moved at least partially and/or substantially completely into the locking bar). For example, when the locking bar is moved in the direction of the locked position, it can be supported on the beveled sides of the pawls and thus be moved into the locking bar (e.g., may not prevent a movement of the locking bar in the direction of the unlocked position).

For example, the fastening unit may have a connection unit for fastening the fastening unit to a leg section interface of an operating table, wherein this connection unit may comprise a snap-in mechanism for fastening to the operating table. For example, an additional actuation element that is arranged on the underside of the fastening unit (e.g., a button) may be provided for releasing the snap-in mechanism. The connection unit can thus be fastened in a simple manner in interfaces that are provided (e.g., already provided) on the operating table. In particular, these interfaces may allow a variation of the angular position of the device for supporting the patient relative to the operating table. By varying the angular position of the device, the height of the receptacle for receiving the coupling element can also be varied relative to a central portion of the operating table.

The snap-in mechanism may comprise, for example, a ball that engages in a complementary recess on the operating table. Furthermore, the connection unit may additionally comprise a pin which is introduced into a recess of the operating table and which may substantially prevent a twisting of the fastening unit.

In addition, the fastening unit may comprise an RFID chip by which it can be identified (e.g., substantially unequivocally identified).

The above-described operating-table-side fastening units may be operated in a simple manner, for example, by a person without time pressure. Since two interfaces may be actuated separately from one another, the probability of an inadvertent release is reduced (e.g., significantly reduced). The arrangement of the actuation element on the underside of the fastening unit may not protrude in an unsuitable manner into the work area (e.g., may not be prone to inadvertent releasing). Also, for example, fastening units with similar operability can be used both for a left rail and also for a right rail of the device for supporting the patient. Thus, production may be made more cost effective.

The described ratchet mechanism may allow a locking and unlocking using similar operation (e.g., by actuating the actuation element in a similar direction, for example, a substantially same direction). The actuation as a downward pull may be ergonomically suitable.

The automatic locking both during coupling and/or uncoupling (e.g., during feeding in and/or removal of the coupling element) may streamline and simplify user operation.

Also for example, an exemplary device-side fastening unit for fastening a device for supporting a patient to be x-rayed to an operating table may comprise a mounting unit fastenable to the device and an intermediate piece rotatably fastened to this mounting unit rotatably, relative to the mounting unit, about a rotation axis. For example, on the intermediate piece, a coupling element for the introduction into a receptacle of an operating-table-side fastening unit may be provided. Furthermore, for example, the intermediate piece may have a plate, which may bear against a plate of the mounting unit, wherein the two plates may be braced against one another and may enable a twisting relative to one another. The plate of the intermediate piece may have two recesses which may be arranged at the same distance from the rotation axis, but on opposite sides of the rotation axis (e.g., may be arranged in a point-symmetric arrangement with respect to the rotation axis). The plate of the mounting unit may also have a recess which is at a similar or same distance from the rotation axis as the two recesses of the intermediate piece. The coupling element of the intermediate piece may be arranged offset relative to the rotation axis (e.g., the rotation axis and the longitudinal axis of the coupling element may not intersect). For example, depending on how the intermediate piece is rotated relative to the mounting unit, the coupling element may be arranged relative to the mounting unit in a different position (for example, at a different height) so that height adjustment may be simplified.

For example, the coupling element may be designed (e.g., for variety) so that it is configured to be complementary relative to the receptacle of the above-described operation-table-side fastening unit and to be receivable in this fastening unit.

In at least some exemplary embodiments, the coupling element may be configured as a rod, a ball or a ring.

The mounting unit may comprise a bolt receptacle, wherein the intermediate piece may have a bolt which is mounted rotatably in this receptacle, wherein the longitudinal axis of the bolt forms the rotation axis. On the end of the bolt facing away from the intermediate piece and protruding from the bolt receptacle, an element substantially preventing the bolt from moving out of the bolt receptacle may be arranged. Thus the rotatability between the mounting unit and the intermediate piece may be implemented in a relatively simple manner and the intermediate piece may be substantially undetachably fastened to the mounting unit.

In at least some exemplary embodiments, in a first mounting position, the intermediate piece may be rotated relative to the mounting unit in such a manner that the recess of the plate of the mounting unit may overlap with one of the recesses of the intermediate piece (e.g., so they are arranged coaxially relative to one another).

Also for example, in a second mounting position, the recess of the plate of the mounting unit may overlap with the other recess of the plate of the intermediate unit. The intermediate piece may be rotated between these two mounting positions, e.g. by about 180° relative to the mounting unit. As a result of this arrangement of the coupling element relative to the rotation axis, for example, in one of the two mounting positions with substantially unchanged alignment of the mounting unit, the coupling element may be arranged above the rotation axis and in one case below the rotation axis. As a result, the relative height between the device and the operating table can be varied. For example, a height variation between 5 and 9 cm, e.g. by approximately 7 cm, can thus occur.

The mounting unit may comprise, for example, a spring bolt for preventing a twisting of the intermediate piece relative to the mounting unit. The spring bolt may be arranged on the opposite side of the mounting unit from the intermediate piece, e.g. behind the borehole of the mounting unit. The spring bolt may comprise a bolt which is preloaded by a spring in a substantially secure position. In this secure position, the bolt may extend through both recesses that overlap with one another (e.g., through both the recess of the mounting unit and the recess of the intermediate piece) so that the set alignment between the mounting unit and intermediate piece (e.g., either the first or the second mounting position) is maintained. Accordingly, for example, no inadvertent twisting may occur. The bolt may be movable by hand (e.g., by an operator) against the spring force into a twisted position in which it at least no longer protrudes into the recess of the intermediate piece, so that the intermediate piece can be twisted manually between the first and the second mounting position.

By using the device-side fastening unit, a rapid and uncomplicated varying of the height of the device relative to the operating table may be achieved, so that the suitable support can be adapted to the individual anatomy of a patient. Also for example, when a highest operating position (e.g., relatively highest suitable position) has been assumed, a C-arc of an x-ray apparatus can still be moved under the device even in the lowest operating position of the operating table, so that an x-ray image can be recorded.

Moreover, via the adjustment, a compact low-height overall construction is achieved.

The device comprises, for example, two rails, on which the device-side fastening units can be attached.

In another exemplary embodiment, a fastening arrangement for fastening a device for supporting a patient, who is to be x-rayed, during an operation to the operating table, may comprise at least one operating-table-side fastening unit of the above-described type and also at least one device-side fastening unit of the above-described type. In the case of the combination of these two fastening units adjusted to one another, an adjustability with simple and suitable operability may be achieved.

In another exemplary embodiment, a device for supporting a patient, who is to be x-rayed, during an operation, may include two device-side fastening units and two operating-table-side fastening units. The device for supporting the patient may have two rails, wherein in each case a device-side fastening unit may be attached to each one of the rails. The two operating-table-side fastening units may be attached to the operating table. The device-side fastening unit arranged on the first rail may engage with a first of the operating-table-side fastening units, and the device-side fastening unit attached to the second rail of the device may accordingly engage with the second operating-table-side fastening unit.

Because, for example, the rails in each case are fastened exclusively via the respective fastening units to the operating table, and because the two operating-table-side fastening units may be released individually, a cross connection between the fastening units may not be suitable. Thus, in the area arranged between the rods, a relatively small amount of material is arranged, so that relatively few contours appear during the x-raying. In addition, the individual independent fastening of the two rails to the operating table may allow for suitable angling (e.g., a relatively large degree of angling) of the operating-table-side fastening units relative to the operating table, so that a corresponding height adjustment can be implemented.

For example, the two operating-table-side fastening units may not be connected directly by a connection unit. Similarly, the two device-side fastening units may also not be connected directly to one another via a connection unit. For example, a direct connection (e.g., an element connecting the two fastening units to one another, so that the fastening units form a single piece) may not be suitable in at least some exemplary embodiments.

The operating-table-side fastening units may be formed, for example, analogously to at least some exemplary embodiments of the above-described operating-table-side fastening units.

Similarly, the device-side fastening units may be formed in accordance with at least some exemplary embodiments of the above-described device-side fastening units. In at least some exemplary embodiments of the above-described fastening units, a cross connection between the fastening unit, e.g. as operating element, can be omitted (e.g., there may be relatively fewer contours in the area of the interface support, so that the area that can be x-rayed is enlarged). For example, the proportion of metal structures that stand out in x-ray images may be reduced.

In addition, the fastening by the above-described operating units may provide for suitable angling (e.g., a relatively large amount of angling) between the device and the operating table. For example, an increased expansion and/or spreading of the vertebrae and better access to the tissue concerned can be achieved. In particular, a patient support in the "Z" position may be provided. In addition, a setting of the angle during the operation may be possible while preserving sterility. Furthermore, relatively more space may be available to place the C-arc of an x-ray apparatus, which may allow suitable operation of the unit.

BRIEF DESCRIPTION OF THE DRAWINGS

Additional features and advantages of the present disclosure are explained further below using the exemplary embodiments illustrated in the below figures.

DETAILED DESCRIPTION AND INDUSTRIAL APPLICABILITY

Figure 1:
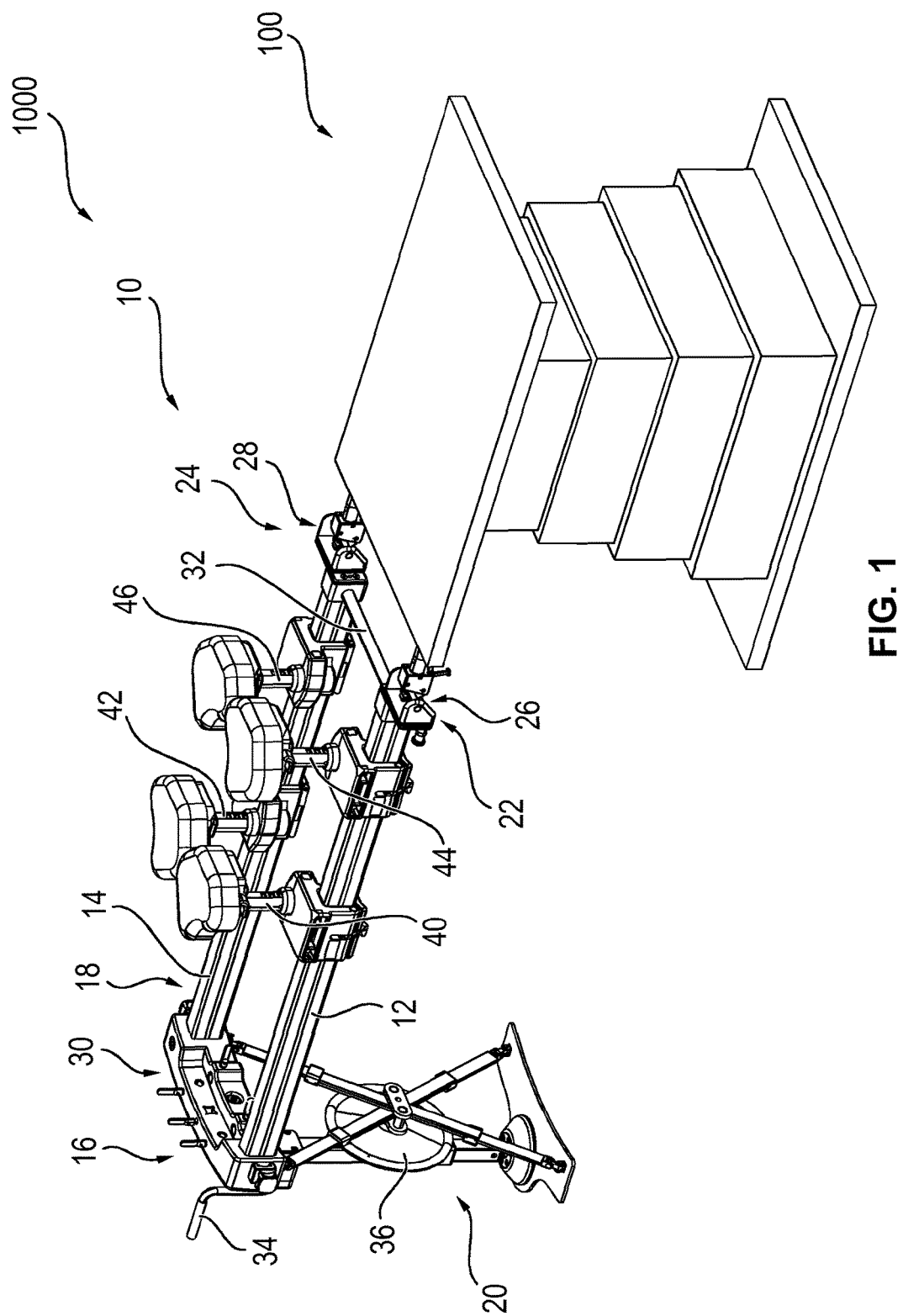
FIG. 1 shows a diagrammatic perspective representation of an exemplary arrangement for supporting a patient during back surgery.
Figure 2:
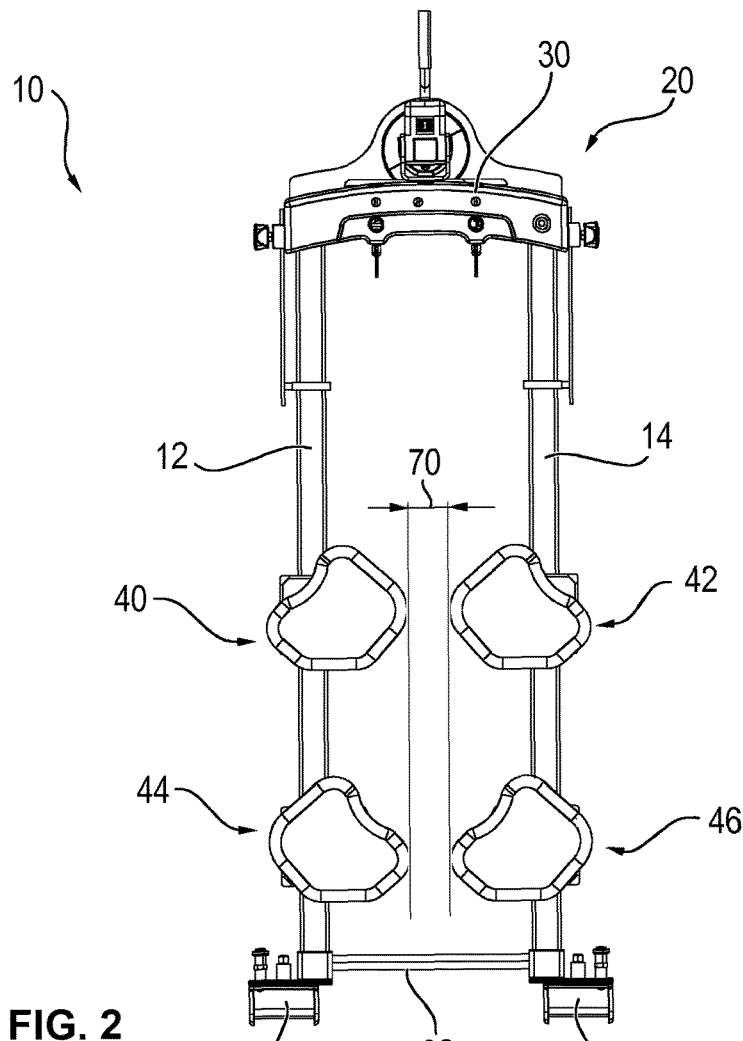
FIG. 2 shows a top view of an exemplary device for supporting a part of the patient of the arrangement according to FIG. 1.

In FIG. 1, a diagrammatic perspective representation of an exemplary arrangement 1000 for supporting a patient during an operation is represented. The arrangement may comprise an operating table 100 as well as a device 10 for supporting the body area of the patient that is to be x-rayed. FIG. 2 shows a top view of this device 10 according to FIG. 1.

In at least some exemplary embodiments, the device 10 may be used to support a patient during back surgery. In such back surgeries, in particular spinal surgeries, the patients as a rule have to be x-rayed during the operation, for which purpose a C-shaped x-ray apparatus may be used. For example, the C-arc of the x-ray apparatus may be moved around the patient for recording 3D images. As will be explained in further detail below, the device 10 may be configured so that it can be used to generate a suitable (e.g., qualitatively high-value) x-ray image in a simple manner. A patient may not be suitably supported on a conventional operating table, because such an operating table does not allow for x-raying with suitable quality and in the required areas. On the one hand, the (e.g., massive) foot column of an operating table may not provide for suitable x-raying length, and a conventional operating table may include an unsuitable amount of metal-containing construction elements that do not provide for suitable x-ray imaging. In addition, the patient-supporting surface of a conventional operating table may be too wide for the recording of 3D views by a C-arc.

The device 10 may comprise two rails 12, 14, the first ends 16, 18 of which may be mounted on a stand 20. The second ends 22, 24 of the rails 12, 14, which may be opposite from the first ends 16, 18, can be fastened via fastening units 26, 28 (e.g., operating table fastening devices) to the operating table 100 (e.g., to interfaces for connecting the operating table 100 to leg sections).

The stand 20 may be used, for example, for supporting the rails 12, 14 on the floor and for providing for a predetermined distance between the rails 12, 14 (e.g., in that the stand 20 may comprise a connection unit 30 by which the two first ends 16, 18 of the rails 12, 14 may be connected to one another).

Similarly, the second ends 22, 24 of the rails 12, 14 may be connected to one another via another connection unit 32, so that a suitable distance (e.g., a predetermined distance or a desired distance) between the rails 12, 14 is maintained. The rails 12, 14 may extend parallel to one another.

The stand 20 may be configured so that it is height-adjustable (e.g., so that the distance of the rails 12, 14 from the floor can be varied). For this purpose, the stand 20 may comprise, for example, a hand crank 34 by which the height can be varied, and a hand wheel 36 for fixing and stiffening the foot of the stand 20.

The operating table to which the rails 12, 14 are fastened via the fastening units 26, 28 may be height-adjustable by an actuator, so that the rails 12, 14 can be arranged horizontally at a suitable height, by setting the stand 20 and the operating table appropriately.

Figure 3:
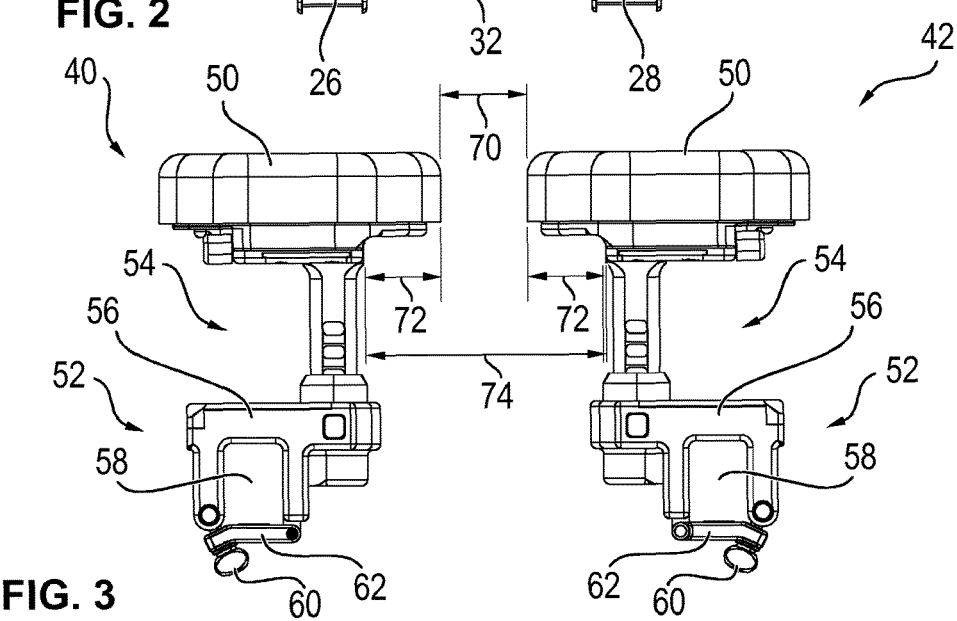
FIG. 3 shows a side view of exemplary patient-supporting units of the device according to FIG. 2.

In at least some exemplary embodiments, two patient-supporting units 40 to 46 for supporting the patient may be arranged on the rails 12, 14. In FIG. 3, two of these patient-supporting units 40, 42 are represented in a side view, wherein, for the simplification of the representation, the rails 12, 14 are not represented.

The patient-supporting units 40 to 46 may each comprise a resting pad 50 on which the patient rests. Furthermore, the patient-supporting units 40 to 46 may each have a fastening unit 52 for fastening the respective patient-supporting unit 40 to 46 to the respective rail 12, 14 as well as a height adjustment unit 54 by which the resting pad 50 may be connected to the fastening unit 52 and by which the distance between the resting pad 50 and the fastening unit 52 can be set.

The fastening unit 52 may comprise a U-shaped base body 56 in the recess 58 of which the respective rail 12, 14 can be received. On the open end of the U-shaped base body, locking bar 62 that is lockable by a screw 60 may be provided. For the mounting of the patient-supporting unit 40 to 46, the fastening unit 52 may be put on the respective rail 12, 14 with the locking bar 62 open, so that this rail may be received in the U-shaped recess 58. Subsequently, the locking bar 62 may be closed and secured by the screw 60, so that a secure and nevertheless simple and rapid fastening of the patient-supporting unit 40 to 46 to the rails 12, 14 may be provided.

The patient-supporting units 40, 42 may be used in particular for supporting a patient's torso, while the patient-supporting units 44, 46 may be used for supporting the patient's hip. Thus, the patient's head may lie in a direction of the stand 20, while the patient's legs may rest on a portion of the patient-supporting surface of the operating table 100 itself. For supporting the head, it is also contemplated that additional patient-supporting units may also be fastened to the rails 12, 14.

The patient-supporting units 40, 44 may be fastened exclusively to the first rail 12, and the patient-supporting units 42, 46 may be fastened (e.g., exclusively) to the second rail 14. There may be no connection between the patient-supporting units 40 and 42 as well as 44 and 46, which may be arranged next to one another.

The patient-supporting units 40 to 46 may be individually slidable independently of one another on the rails 12, 14, so that, together with the height adjustment of the patient-supporting units 40 to 46, a suitable adaptation to the individual anatomy of a patient to be operated on is provided. For example, the patient-supporting units 40 to 46 may also be arranged away from each other (e.g., in any suitable location in addition to being disposed, e.g., directly next to one another). In addition, the resting pads 50 can be arranged at different heights. Furthermore, the distance between the resting pads 50 of adjacent patient-supporting units 40 and 42 as well as 44 and 46 can be varied, in that, accordingly, the resting pads may be slidably mounted transversely on the height adjustment unit 54.

As illustrated in FIGS. 2 and 3, the distance between the rails 12 and 14 and the dimensions of the patient-supporting units 40 to 46 may be selected so that a space (e.g., a free space) is formed between the sides facing one another of the resting pads 50 fastened on different rails 12, 14. By this spacing of the resting pads 50 and by not connecting the patient-supporting units 40, 42 and 44, 46, it is achieved that a substantially material-free x-ray area is formed, which is indicated in FIG. 2 with a rectangle and marked with the reference numeral 70. In this substantially material-free x-ray area 70, the x-rays may not be influenced by any material, so that a suitable x-ray image is possible, particularly if the patient's vertebral column is suitably (e.g., correctly) supported in this area.

The resting pads 50 of the patient supporting units 40 to 46 may be formed, in particular, from a substantially x-ray permeable material, for example, from a carbon-fiber-reinforced plastic. In addition, the shape thereof may be configured to be relatively homogeneous and thin in an area adjoining the x-raying area, in order to reduce or substantially prevent x-ray radiation absorption differences that would be reproduced in an x-ray image. Thus, at least in the areas in which they protrude from the fastening unit 52 and the height-adjustment unit 54 in the direction of the x-ray area 50, the resting pads 50 may be highly permeable to x-rays so that, as shown in FIG. 3, in each case an additional x-ray area 72 is obtained (e.g., in which an x-ray image with suitable quality can be recorded). Together with the x-ray area 70, the result may be an enlarged x-ray area 74 that can be used during the operation.

The fastening unit 52 and the height adjustment unit 54 may be configured so that they protrude only as little as possible over the rails 12, 14 in the direction of the x-ray area 70, so that a suitable (e.g., a relatively large) additional x-ray area 72 is formed and thus the enlarged x-ray area 74 is relatively large.

The above-described device 10 may thus allow, for example, suitable flexibility in adapting to the individual anatomy of a patient and the recording of x-ray images of suitable quality.

Figure 4:
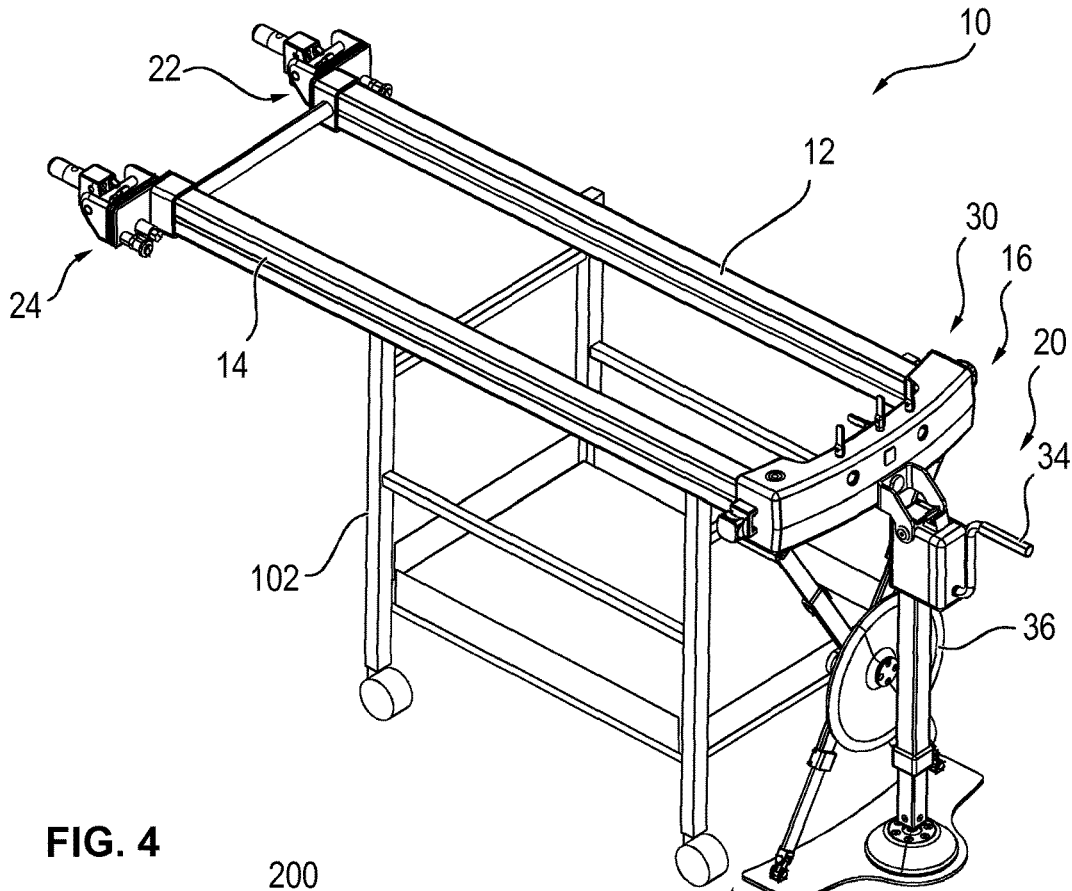
FIG. 4 shows a diagrammatic perspective representation of the exemplary device according to FIG. 2 in a disassembled state.

In FIG. 4, a diagrammatic perspective representation of the device 10 according to FIG. 2 is shown (e.g., as a disassembled state) in which the device 10 may not be connected to the operating table 100. Instead, the rails 12, 14 may be supported on a movable carriage 102, so that the device 10 can be moved to its destination site in a simple manner.

Figure 5:
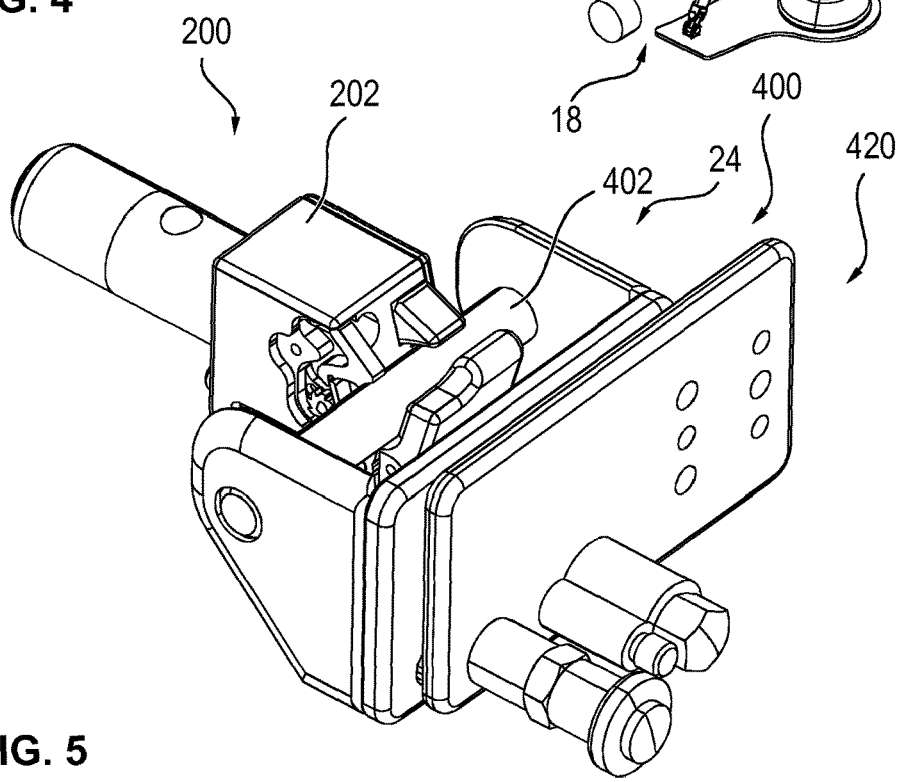
FIG. 5 shows a diagrammatic perspective representation of a fastening arrangement for fastening the exemplary device according to FIGS. 2 and 4 to an operating table.

In FIG. 5 a diagrammatic perspective representation of the fastening arrangement 26 is represented, by which the first rail 12 is connected to the operating table 100. The second fastening unit 28 may be constructed, for example, similarly so that it may be used in combination with the below-described exemplary embodiments.

The fastening arrangement 26 may comprise an operating-table-side fastening unit 200, which can be fastened to interfaces for receiving leg sections of the operating table 100, as well as a device-side fastening unit 400 (e.g., a device-side fastening assembly) which can be fastened to the two ends 22, 24 of the rails 12, 14 (e.g., wherein the device-side fastening unit 400 may be, e.g., a rail-side fastening unit 400). Via the fastening arrangement 26, the respective rail 12, 14 can be detachably fastened to the operating table 100 in a relatively simple manner.

Figure 6:
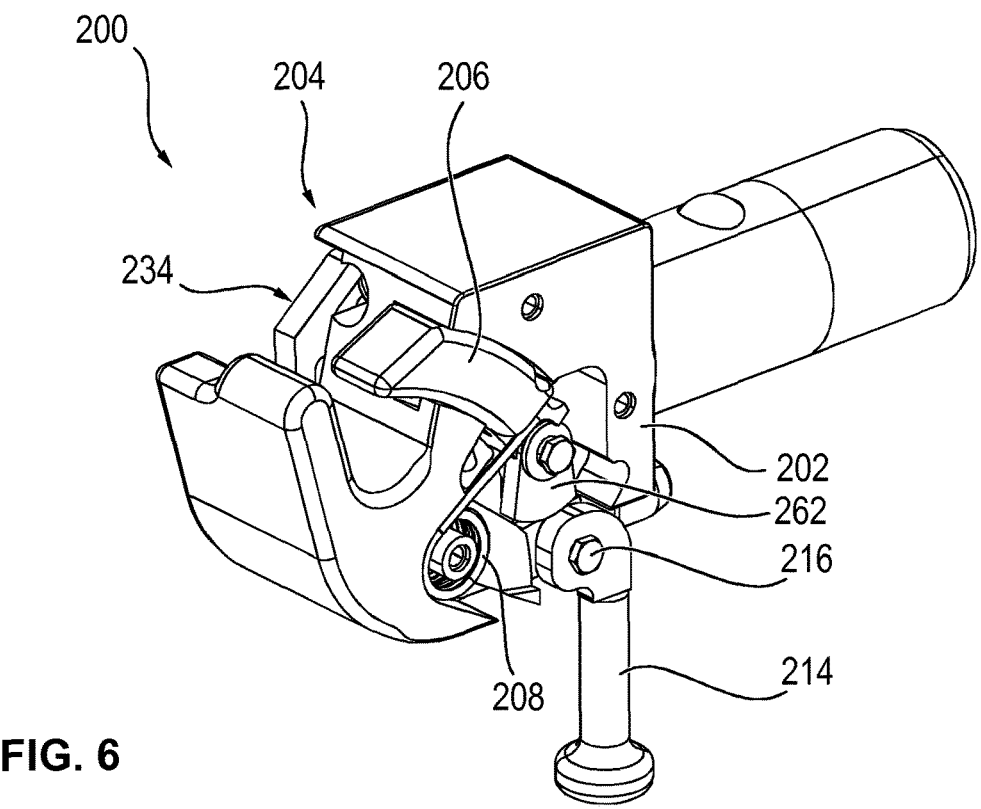
FIG. 6 shows a diagrammatic perspective representation of an exemplary operating-table-side fastening unit of the fastening arrangement according to FIG. 5.
Figure 7:
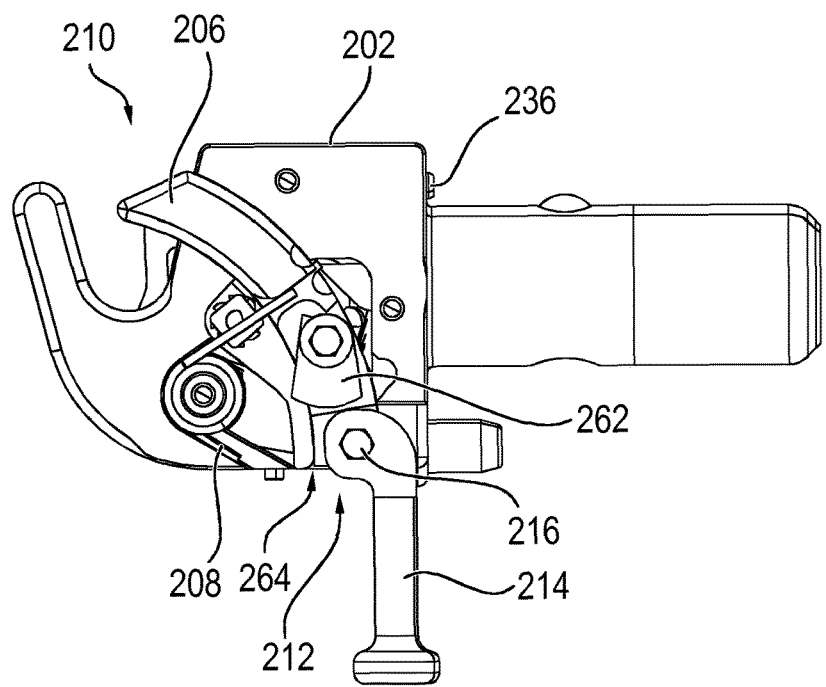
FIG. 7 shows a side view of the exemplary fastening unit according to FIG. 6.
Figure 8:
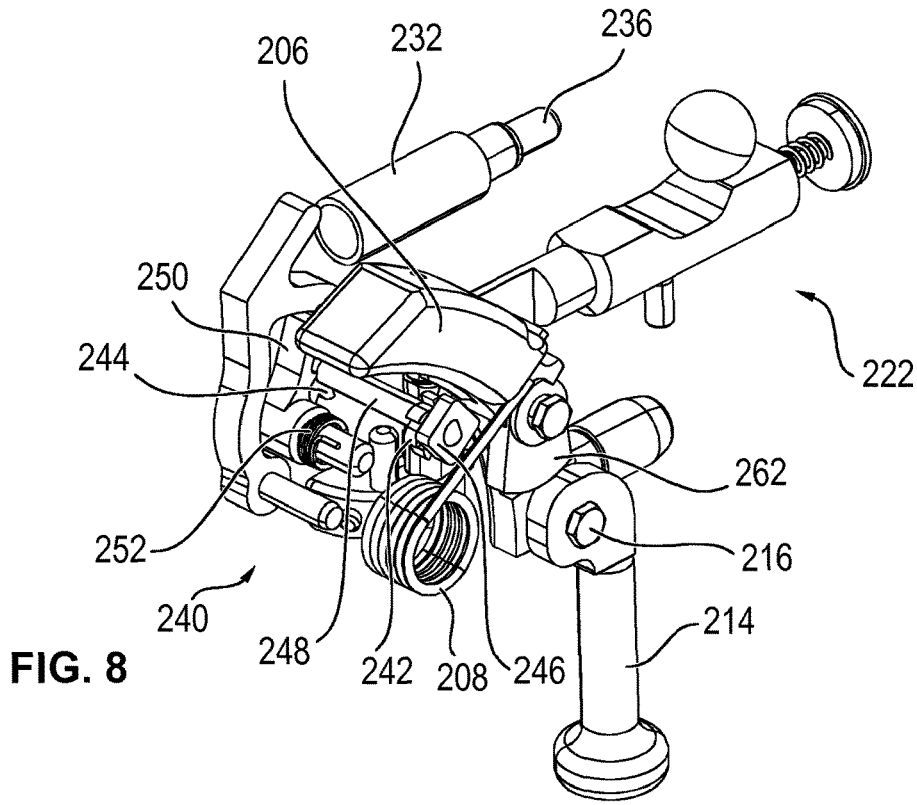
FIG. 8 shows a diagrammatic perspective representation of the interior components of the exemplary fastening unit of FIGS. 6 and 7.

In FIGS. 6 to 13, for example, the operating-table-side fastening unit 200 is illustrated. For example, as illustrated in FIG. 5, the representation of lateral coverings of the housing may be omitted in order to represent the interior components. In FIG. 8, additionally for example, for the representation of a base body 202, the fastening unit 200 is omitted in order to improve the visibility of the interior components.

In the various figures, described operating states are represented partially, and are further explained below, after the description of the construction, in connection with the description of the function.

The fastening unit 200 may comprise the base body 202 (e.g., a housing or a structural housing) which is used for supporting the components to be described in further detail below. The base body 202 may have a V-shaped receptacle 204, in which a coupling element (e.g., a coupler such as, for example, a structural member of any suitable shape for mechanical coupling such as a rod 402) of the rail-side fastening unit 400 can be received, in order to thereby attach the rails 12, 14 accordingly.

Figure 9:
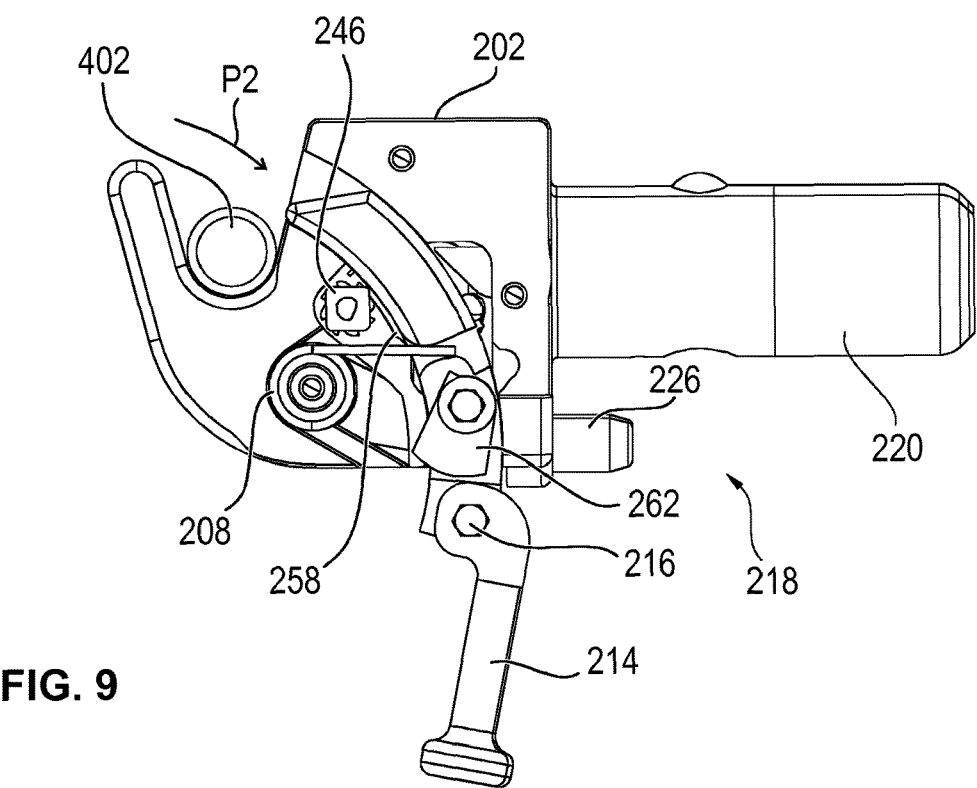
FIG. 9 shows a side view of the exemplary fastening unit of FIGS. 6 to 8 in an additional operating state.
Figure 11:
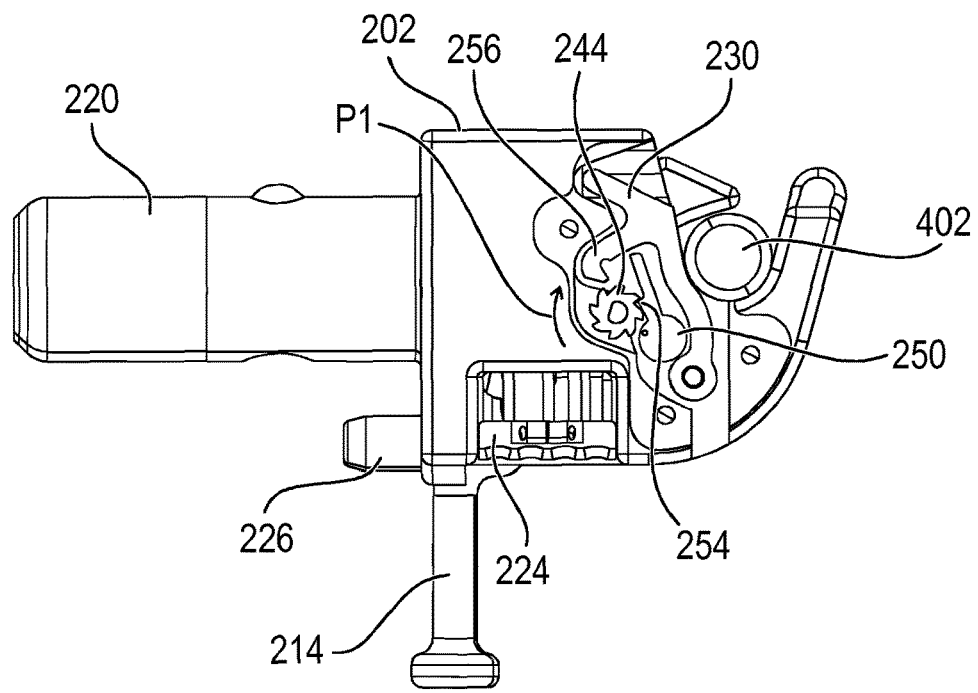
FIG. 11 shows a side view of the exemplary fastening unit according to FIGS. 6 to 9 with a view onto the side opposite from the side view of FIGS. 7 and 9.

The fastening unit 200 furthermore may comprise a locking bar 206 (e.g., a locking member), which is movable between a locked position represented in FIGS. 6, 7 and 11 and an unlocked position, relative to the base body 204, shown in FIG. 9. The locking bar 206 may be preloaded via a torsion spring 208 (e.g., a resilient member) in the locked position (e.g., locking bar 206 is urged by torsion spring 208 into or toward the locked position, and/or locking bar 206 is urged by torsion spring 208 to remain in the locked position) and can be moved against the resetting force of this torsion spring 208 into the unlocked position.

In the locked position, a first end 210 of the locking bar 206 may protrude into the recess 204 so that, as represented in FIG. 11, the rod 402 may not be removed from the recess 204 (e.g., unless the locking bar 206 has been moved beforehand into the unlocked position).

For moving the locking bar 206, on the second end 212 opposite the first end, a pull lever 214 (e.g., any suitable element or member for actuating such as a mechanical actuation assembly or mechanical actuation member) may be arranged as an actuation element. For example, this actuation element may be rotatably attached relative to the locking bar via a pin and a nut 216, so that the pull lever 214 can be folded relative to the base body 202 (e.g., and thus may extend minimally into the work area). The arrangement on the underside of the fastening unit 200 may also have the effect that the lever 214 may not be actuated inadvertently (e.g., so that it can be operated in an ergonomically suitable manner).

Furthermore, the fastening unit 200 may comprise a connection unit 218 (e.g., a connection member), by which the fastening unit 200 can be fastened to the operating table 100. The rod 220 may be introduced in a corresponding recess of the operating table 100 and may engage via a snap-in mechanism 222 in the interface of the operating table 100 (e.g., so that the fastening unit 200 may not be released inadvertently). On the underside of the fastening unit 200, a connection device (e.g., button 224) may be arranged, by which the snap-in connection can be released again, so that the fastening unit 200 can be removed from the operating table 100.

Furthermore, the connection unit 218 may comprise a pin 226, which may engage in a corresponding recess of the operating table and may thus prevent a twisting about the longitudinal axis of the rod 220.

In addition, the fastening unit 200 may comprise a feeler member (e.g., a feeler 230) which may be preloaded via a resilient element 232 (e.g., a resilient member 232) in a first position (e.g., feeler 230 may be urged via the resilient element 232 in or toward the first position) shown in FIGS. 6 and 7, in which it may protrude into the recess 204. If a rod 402 is introduced into the recess 204, then this rod may come in contact with the feeler 230 on the beveled surface 234 thereof and move the feeler 230 from the first position into a second position represented in FIGS. 9 and 11 (e.g., in which the feeler 230 no longer protrudes into the receptacle 204). As long as the rod 402 is received in the receptacle 204, this rod may hold the feeler 230 in the second position. During the movement from the first position into the second position, a silicone block 236, on the side of the fastening unit 200 facing the operating table 100, may be moved out of this fastening unit so that play present between the operating table 100 and the fastening unit 200 is reduced (e.g., minimized).

In addition, the fastening unit 200 may have a ratchet assembly or ratchet mechanism 240 (e.g., an suitable assembly that performs ratcheting such as, for example, a mechanical ratchet assembly or a mechanical ratchet mechanism) by which the locking bar 206 can be held under certain operating conditions in the unlocked position (for example, ratchet mechanism 240 may maintain or hold locking bar 206 in the unlocked position).

This ratchet mechanism 240 may comprise a first ratchet wheel 242, a second ratchet wheel 244, a square washer 246, a shaft 248 as well as a blocking element 250 (e.g., a blocking member). The ratchet wheels 244 as well as the square washer 246 may be arranged in a torsion-proof manner on the shaft 248, so that the unit formed therefrom can be rotated jointly (e.g., only rotated jointly). The blocking element 250 may be preloaded via a torsion spring 252 in a blocking position shown in FIG. 11. In this blocking position, a protrusion 254 of the blocking element 250 may engage in a notch of the second ratchet wheel 244 and thereby may substantially prevent a rotation of the second ratchet wheel 244 in a first rotation direction P1. The shape of the ratchet wheel 244 and the shape of the blocking element 250 may be adapted to one another in such a manner that a rotation against the first direction P1 (e.g., in a direction opposing the first direction P1) is possible depending on the position of the blocking element 250.

If the feeler 230 is arranged in the first position, then, by the contact between a nose 256 and the element 250, the feeler 230 may hold this element in a released position (e.g., in which it is no longer in engagement with the second ratchet wheel 244 and thus the second ratchet wheel 244 and consequently the shaft 248 and the other components mounted on it may also be rotatable in the first direction P1).

Since, as described above, the feeler 230 may be preloaded in the first position, the blocking element 250 may be arranged in the released position as long as rod 402 is not received in the receptacle 204. Also for example, if a rod 402 is received in the receptacle 204, then the feeler 230 may be moved into the second position, so that the blocking element 250 is arranged in the blocking position.

Thus, when rod 402 is not received in the receptacle 204, the shaft 248 may be rotatable in the first direction, so that the ratchet mechanism 240 is released. Also for example, if a rod 402 is received in the receptacle 204, the blocking element 250 may block a rotation of the shaft 248 in the first direction P1, so that the ratchet mechanism 240 may be blocked.

Figure 10:
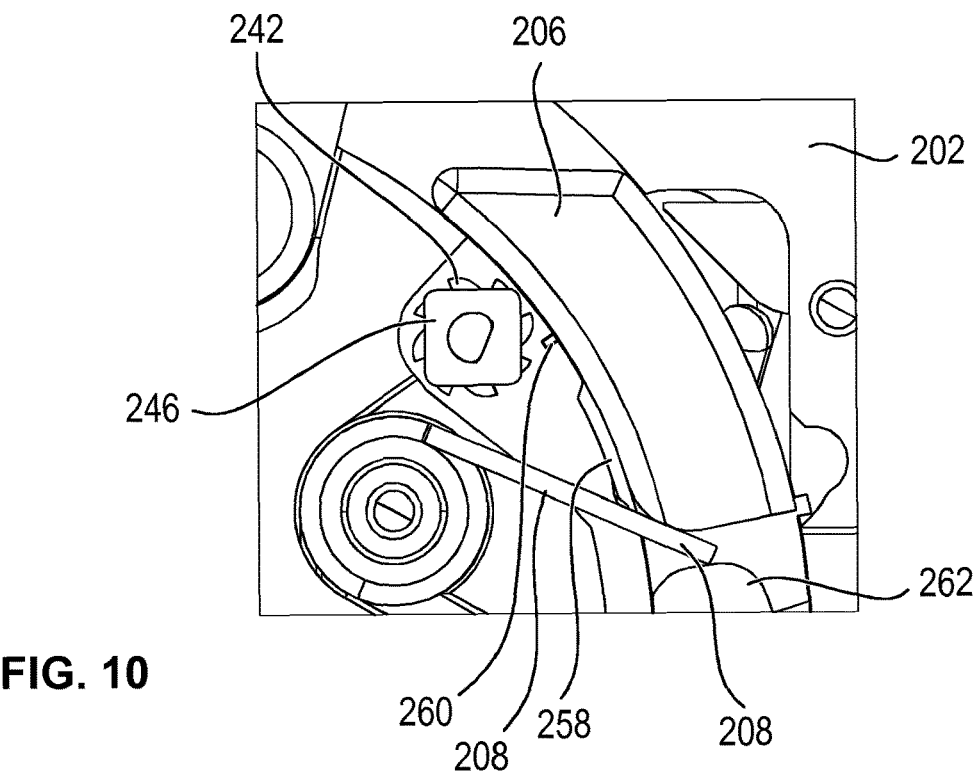
FIG. 10 shows a detail of the exemplary fastening unit according to FIGS. 6 to 9.

Depending on the rotational position of the shaft 248, the square washer 246 may be arranged either in a blocking angular position or in an unblocking angular position. An exemplary unblocking angular position is illustrated in FIG. 7, and an exemplary blocking angular position is illustrated in FIGS. 9 and 10. The shapes of the first ratchet wheel 242 and the square washer 246 may be adapted to one another in such a manner that, when the first ratchet wheel 242 is rotated by one more notch against the first rotation direction P1, the position of the square washer 248 alternates between the blocking angular position and the unblocking angular position.

On the locking bar 206, a protrusion 258 may be formed, which, if the square washer 246 is arranged in the blocking angular position, may engage with this square washer. To the extent that the ratchet mechanism 240 is blocked (e.g., a rotation of the shaft 248 against the direction P1 is substantially prevented), the contact between the protrusion 248 and the square washer 246 may substantially prevent the locking bar 206 from moving from the unlocked position into the locked position (e.g., when the locking bar 206 has been moved further via the pull lever 214 past the unlocked position in the direction of the arrow P2). This state is shown in FIG. 9, for example.

Also for example, if the ratchet mechanism 240 is released, then the shaft 248 may be rotated by the tensioning of the locking bar 206 in the first rotation direction, so that the locking bar 206 would move automatically into the locked position.

Furthermore, in a recess of the locking bar 206, a contact element 260 (e.g., a contact member) may be resiliently mounted. When the locking bar 206 is moved from the locked position into the unlocked position or past this unlocked position (e.g., when the pull lever 214 is completely actuated), then the ratchet wheel 242 may be rotated by one more notch against the first direction P1, so that the square washer 246 is rotated from the unblocking angular position into the blocking angular position. Subsequently, the locking bar 206 may move back again in the direction of the locked position, from the position moved out of the locked position (e.g., FIG. 10), wherein the contact element 260 may then be moved into the locking bar 206 by the contact with the beveled side of the notch of the first ratchet wheel 242 (for example, so that even when the ratchet mechanism 240 is blocked, the locking bar 206 can move in the direction of the locked position until the engagement between the protrusion 258 and the square washer 246 exists, and the locking bar 206 is arranged accordingly in an exemplary unlocked position, as shown in FIG. 9).

As long as rod 402 has not yet been received in the receptacle 204, the feeler 230 may be arranged in the first position, so that the ratchet mechanism 240 may be released. The locking bar 206 may then be arranged in the locked position. Even if the pull lever 214 is actuated, the locking bar 206 may move again back into the locked position because, due to the released ratchet mechanism 240, the shaft 248 may be rotatable in the first direction P1 (e.g., and thus independently of the position thereof, may not hold the locking bar 206 in the unlocked position).

If rod 402 is pressed into the receptacle 204, then, for example, the feeler 230 may be moved from the first position into the second position (e.g., so that the ratchet mechanism 240 may be blocked, and a rotation into the first direction P1 from then on may be prevented as long as the rod 402 is arranged in the receptacle 204). Also for example, with the introduction of the rod 402 through this receptacle, the locking bar 206 may be moved from the locked position in the direction of the unlocked position, but not so far that the protrusion 58 is moved behind the square washer 246 (e.g., but not so far that the locking bar 206 is arranged in the unlocked position). Thus, the locking bar 206, after the rod 402 has passed by, may be again moved automatically back into the unlocked position.

If the rod 402 is to be removed from the receptacle 204, then the locking bar 206 first may be moved from the locked position into the unlocked position. When the pull lever 214 is actuated, the locking bar 206 may be moved past the unlocking position, wherein the first ratchet wheel 242 may be rotated by one more notch against the direction P1, due to the contact via the contact element 260 with the notches of the first ratchet wheel 242. As a result, for example, the square washer 246, e.g., previously arranged in the unblocking angular position, may be moved into the blocking angular position. After the pull lever 214 has been released, the torsion spring 208 may move the locking bar 206 back again until the protrusion 258 engages with the square washer 246. Since the ratchet mechanism 240, as described above, may be blocked, the shaft 248 may not rotate in the first direction P1 (e.g., so that the square washer 246 may not change the orientation thereof and thus the locking bar 206 may be held in the unlocked position, without the pull lever 214 being held fixed for that purpose). If the rod 402 is removed from the receptacle 204, then the feeler 230 may move again back from the second position into the first position, as a result of which the ratchet mechanism 240 is released. Accordingly for example, the shaft 248 can rotate in the first direction P1, as a result of which the square washer 246 can be rotated again from the blocking angular position into the unblocking angular position (e.g., so that this square washer no longer retains the locking bar 206, and the locking bar 206 may move automatically back into the locked position).

If for example, after the (e.g., one-time) actuation of the pull lever 214, the locking bar 206 held by the square washer 246 in the unlocked position is to be locked again without removing the rod 402 (e.g., because the pull lever 214 was actuated inadvertently), the operator may pull again on the pull lever 214. As a result, the locking bar 206 may be moved from the unlocked position further into the base body 202 in the direction of the arrow P2, as a result of which the contact element 260 may move the first ratchet wheel 242 by one more notch. Thus, the square washer 246 may be moved again from the blocking angular position into the unblocking angular position, so that, after the release of the pull lever 214, the protrusion 258 can move past the square washer 246, and thus the locking bar 206 may automatically move again into the locked position. For example, the ratchet assembly (e.g., ratchet mechanism 24) may maintain the locking member (e.g., locking bar 206) in the unlocked position when the coupler (e.g., coupling element 402) is disposed in the receptacle (e.g., receptacle 204) and the locking member (e.g., locking bar 206) has been moved into the unlocked position by a first actuation of the actuation member (e.g., actuation element or pull lever 214). Further, for example, the ratchet assembly (e.g., ratchet mechanism 24) may release the locking member (e.g., locking bar 206) from the unlocked position when either the coupler (e.g., coupling element 402) has been removed from the receptacle (e.g., receptacle 204) or the actuation member (e.g., actuation element or pull lever 214) is actuated a second time The above-described locking mechanism may provide a simple and suitable locking, which is not prone to unsuitable operation and may provide for a streamlined operation (e.g., when rod 402 has been received).

Figure 12:
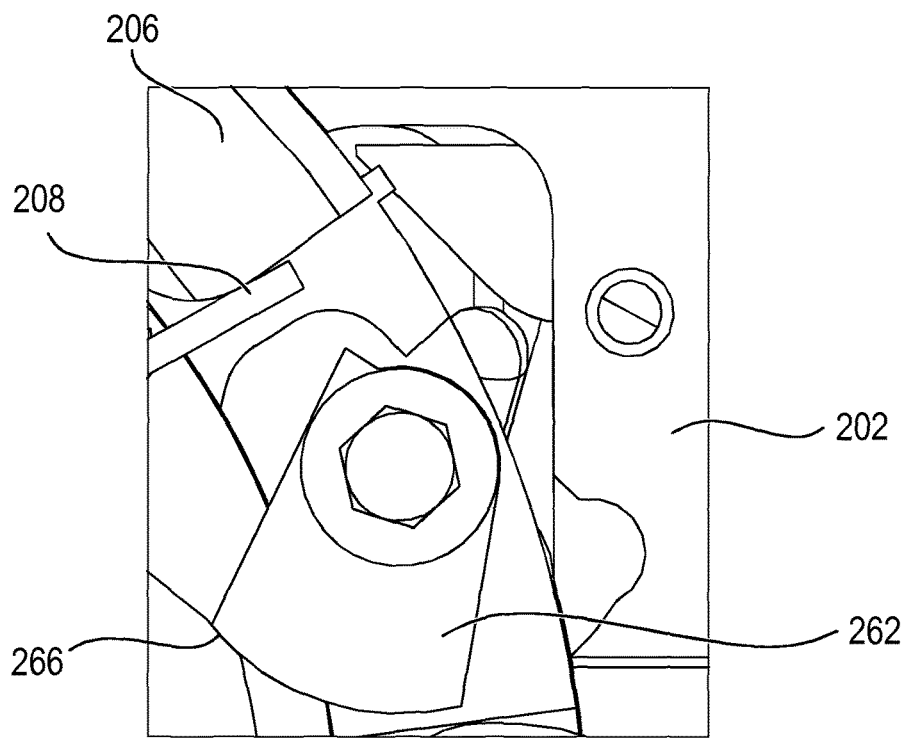
FIG. 12 shows a detail of the exemplary fastening arrangement according FIGS. 7 to 11 in the case of an inclined arrangement.
Figure 13:
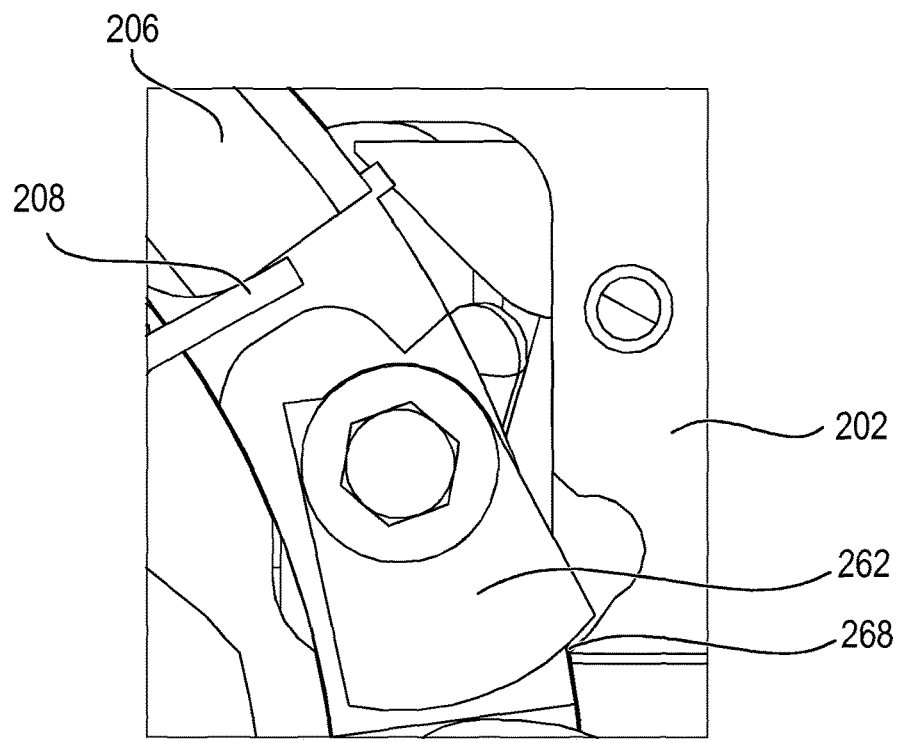
FIG. 13 shows a detail of the exemplary fastening unit according to FIGS. 6 to 11 in the case of an additional inclined arrangement of the fastening unit.

On the locking bar 206, a gravity pendulum 262 may be rotatably mounted, which, when the fastening unit 200 is arranged horizontally (e.g., as shown in FIG. 5, may be oriented so that, when the pull lever 214 is actuated, it may move into an opening 264 and thus may not interfere with the movement of the locking bar 206). Also for example, if the fastening unit 200 is moved out of the horizontal by an angle that is greater than a predetermined limit angle (e.g., as shown in FIGS. 12 and 13, wherein FIG. 12 shows a tilting forward, and FIG. 13 shows a tilting backward), that is in the direction of the OP table, then the gravity pendulum 262 may substantially prevent an actuation of the pull lever 214, since it engages with edges 266, 268 of the base body, and thus may substantially prevent a moving of the locking bar 206.

Via gravity pendulum 262, an unlocking of the locking bar 206 may occur only in an approximately horizontal orientation, so that, for example, when the fastening unit 200 is inclined forward (e.g., away from the operating table 100), the rod 402 may not slip out of the receptacle 204 (e.g., due to an inadvertent release of the unlocking).

Alternatively for example, instead of a ratchet mechanism, other embodiments of a flip-flop mechanism can also be used.

Figure 14:
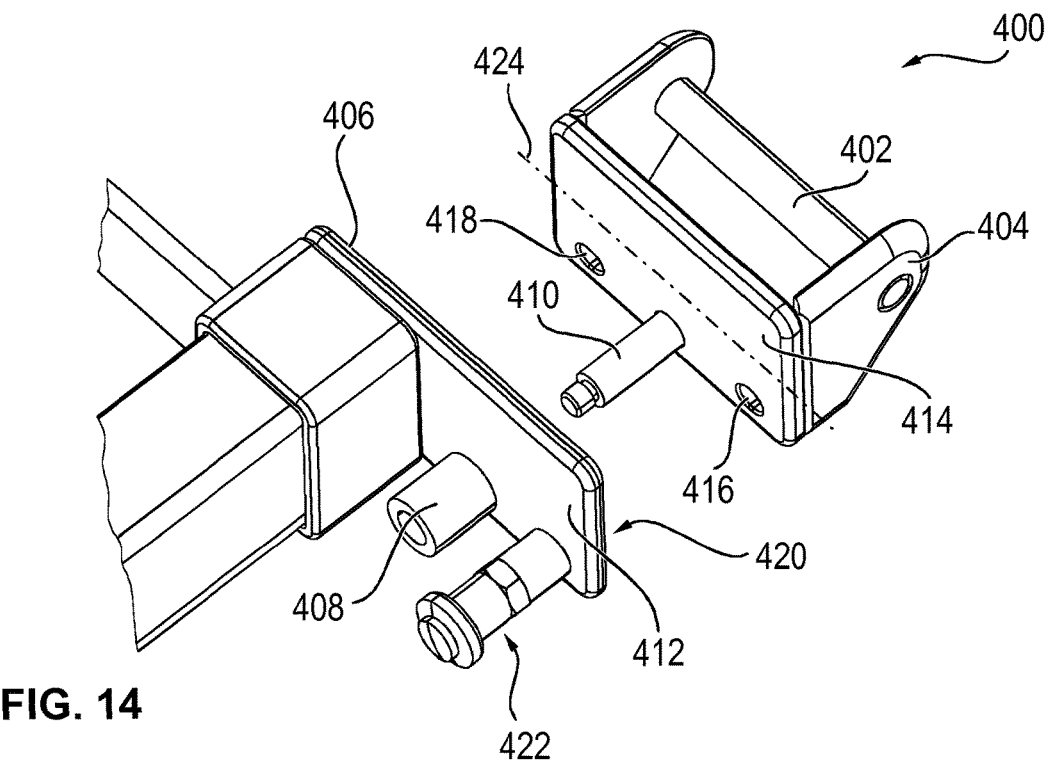
FIG. 14 shows a diagrammatic perspective representation of the device-side fastening unit of the exemplary fastening arrangement according to FIG. 5.
Figure 15:
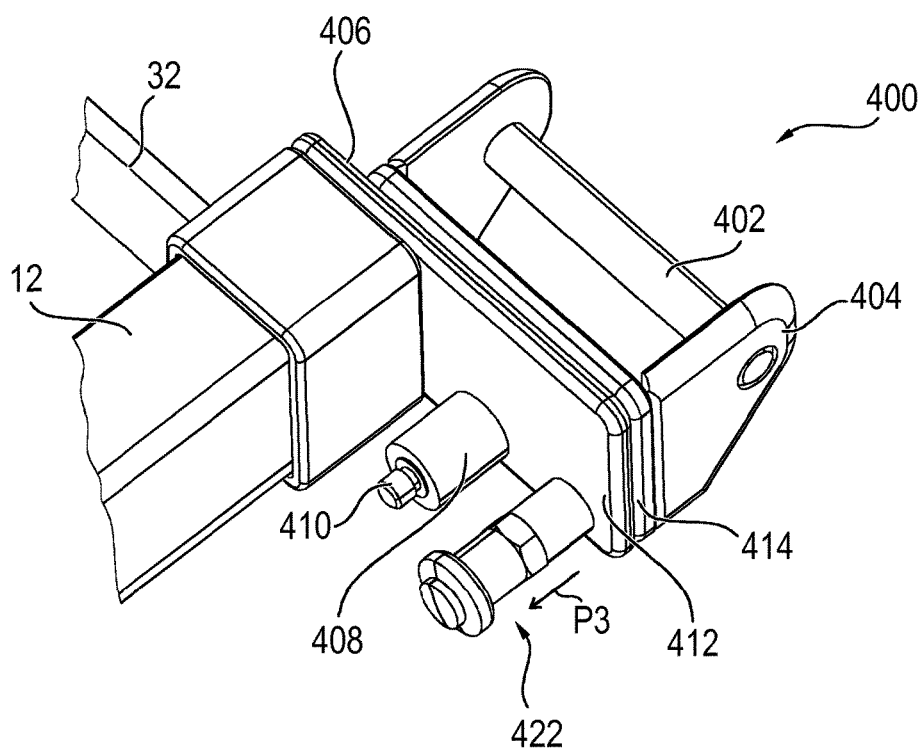
FIG. 15 shows an additional diagrammatic perspective representation of the exemplary fastening unit according to FIG. 14.

In FIGS. 14 and 15, diagrammatic perspective illustrations of the rail-side fastening unit 400 according to FIG. 5 are shown. The rail-side fastening unit 400 may comprise a mount (e.g., a mounting unit 406) which is, for example, durably fastenable to the rails 12, 14, as well as an intermediate piece 404 which may comprise the rod 402. In FIG. 14, the intermediate piece which may be undetachably fastened to the mounting unit 406, is illustrated e.g. as separated from this mounting unit (e.g., as an exemplary illustration of the fastening mechanism).

The mounting unit 406 may comprise a bolt receptacle 408, in which a bolt 410 of the intermediate piece 404 may be mounted, so that the intermediate piece 404 is rotatable relative to the mounting unit 406 (e.g., provided that this is not prevented by a torque-proofing device). On the end of the bolt 410 protruding from the bolt receptacle 408, a securing device may be attached, for example, which may substantially prevent the removal of the intermediate piece 404 from the mounting unit 406.

The mounting unit 406 and the intermediate piece 404 may each comprise a plate 412, 414 which, in at least some exemplary embodiments, may lie against one another and be twisted against one another. Alternatively for example, between the plates 412, 414, a predetermined spacing may also exist, so that these plates are not in contact with one another.

The plate 414 of the intermediate piece 404 may have two boreholes 416, 418, which may be arranged at the same distance from the bolt 410 on the opposite sides of the bolt 410. For example, a line connecting the two boreholes 416, 418 to one another may extend through the longitudinal axis of the bolt 410, wherein this longitudinal axis may intersect the line connecting the boreholes 416, 418 in the center. The boreholes 416, 418 and the bolt 410 may be arranged offset relative to a central axis 424 in a first direction. The rod 402, for example, may also be arranged offset relative to the central axis 424, but in a second direction opposite the first direction. Thus, with reference to the alignment shown in FIG. 14, the boreholes 416, 418 and the bolt 420 may be arranged below the central line 424, while the rod may be arranged above the central line 424.

Alternatively for example, instead of boreholes 410 to 420, other recesses (e.g., holes) can also be provided. For example, the recesses of the plate 414 of the intermediate piece 414 can also be such that they do not pass entirely through.

The plate 412 may also have a borehole 420 which in the exemplary embodiments of FIGS. 14 and 15 may be covered by a spring bolt 422, which may be arranged on the side of the mounting unit 406 facing away from the intermediate piece 404. The borehole 420 may be at the same distance from the bolt receptacle 408 as the boreholes 416, 418 from the bolt 410.

The intermediate piece 404 can be stopped on the mounting unit in, e.g., two different alignments relative to the mounting unit 406. Here, in FIG. 16, a first orientation is shown, and in FIG. 17 a second orientation is shown.

Figure 16:
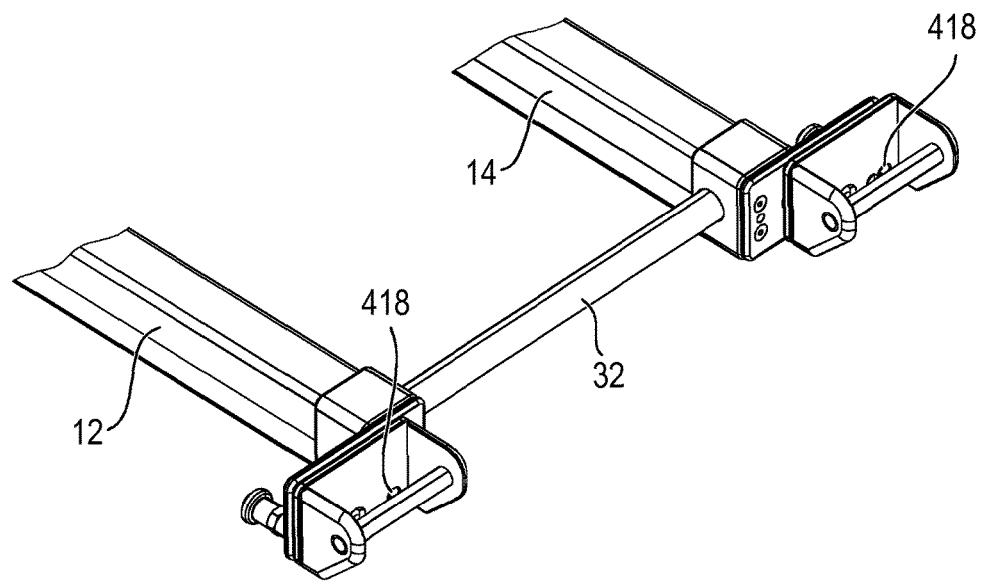
FIG. 16 shows a diagrammatic perspective representation of two exemplary fastening units according to FIGS. 14 and 15 and two exemplary rails in a first mounting position.

In the first orientation shown in FIG. 16, the intermediate piece 404 may be rotated so that the borehole 416 thereof is set coaxially relative to the borehole 420 of the mounting unit 406, so that a bolt of the spring bolt 422 may protrude through these two boreholes 416, 420 which may overlap with one another and thus may substantially prevent a twisting of the intermediate piece 404 relative to the mounting unit 406.

Figure 17:
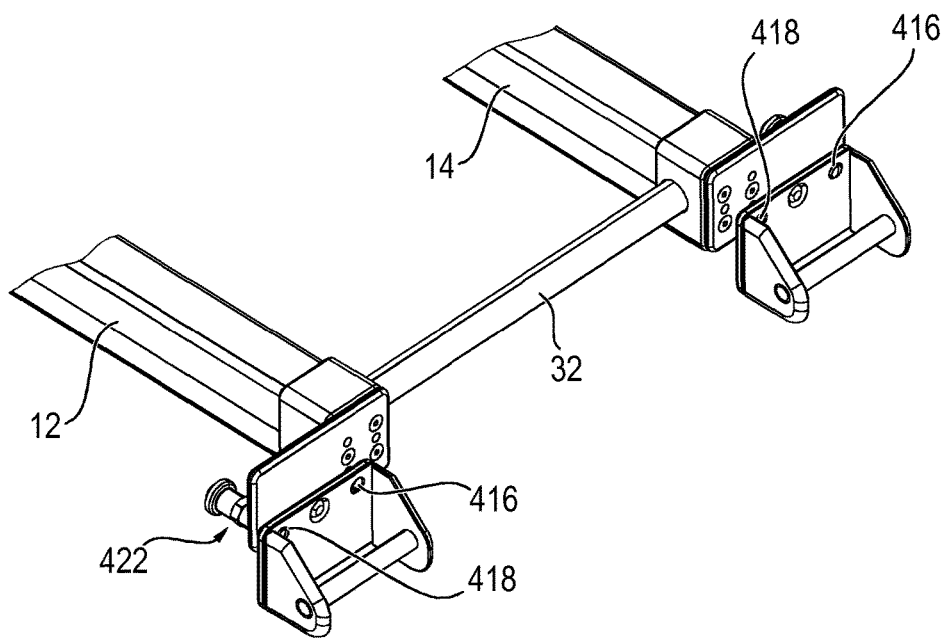
FIG. 17 shows a diagrammatic representation of the exemplary fastening units and of the exemplary rails according to FIG. 16 in a second mounting position.

In the second exemplary orientation shown in FIG. 17, the intermediate piece 404 may be rotated relative to the first orientation by 180° about the longitudinal axis of the bolt 410, so that the borehole 418 and the borehole 420 overlap (e.g., they are arranged coaxially with respect to one another). Accordingly, the bolt of the spring bolt 422 may protrude through these two boreholes and may again prevent a twisting of the intermediate piece relative to the mounting unit 406. By the rotation of the intermediate piece 404 relative to the mounting unit 406, and by the arrangement of the rod 402 offset relative to the rotation axis, the rod 402 may be arranged in the two orientations at a different height relative to the rails 12, 14 (e.g. so that, during fastening to the operation-table-side fastening unit 200, a height adjustment may be accordingly achieved).

For example, a height adjustment of approximately 7 cm can be achieved by rotation of the intermediate piece 404.

In order to change this orientation, for example to rotate the intermediate piece 404, the bolt of the spring bolt 422 may be moved in the direction of the arrow P3 against the spring force of the spring bolt 422 (e.g., so that this spring bolt at least no longer protrudes into the borehole 416 or 418, respectively, of the intermediate piece 404). Thus, when the bolt is retracted, the intermediate piece 404 can be rotated. If the bolt of the spring bolt 422 is released again, then it may again be moved automatically by the spring against the direction P3, so that it protrudes again into the intermediate piece 404 borehole 416, 418 that is arranged in front of the hole 420, and fixes the intermediate piece 404 in the corresponding orientation.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

The invention claimed is:

1. A fastening device for an operating table, comprising:
a housing having a receptacle that receives a coupler of an operating table device;
a locking member connected to the housing and movable relative to the housing between a locked position and an unlocked position, the locking member retaining the coupler in the receptacle in the locked position, and the locking member releasing the coupler from the receptacle in the unlocked position;
a resilient member that urges the locking member toward the locked position;
an actuation member that moves the locking member from the locked position to the unlocked position; and
a ratchet assembly that maintains the locking member in the unlocked position;
wherein the ratchet assembly maintains the locking member in the unlocked position when the coupler is disposed in the receptacle and the locking member has been moved into the unlocked position by a first actuation of the actuation member; and
wherein the ratchet assembly releases the locking member from the unlocked position when either the coupler has been removed from the receptacle or the actuation member is actuated a second time.

2. The fastening device of claim 1, wherein the receptacle is a V-shaped receptacle having a rounded bottom area.

3. The fastening device of claim 1, wherein:
the actuation member includes a traction lever that is rotatably fastened to the locking member, the traction lever being configured to be pulled away from the housing; and
the traction lever moves the locking member from the locked position into the unlocked position and also releases the ratchet assembly, so that when the coupler is received in the receptacle, the locking member is moved back into the locked position by the resilient member.

4. The fastening device of claim 1, wherein a gravitational pendulum is rotatably fastened on the locking member, the gravitational pendulum preventing an actuation of the actuation member when the fastening device is arranged outside of a predetermined alignment area relative to the horizontal.

5. The fastening device of claim 1, wherein:
an end of the locking member protruding into the receptacle is beveled; and
when the coupler protrudes into the receptacle, the locking member is moved out of the locked position and toward the unlocked position based on contact with the coupler, but not far enough for the ratchet assembly to hold the locking member.

6. The fastening device of claim 1, wherein the ratchet assembly is a flip-flop mechanism.

7. The fastening device of claim 1, further comprising:
a connection member that fastens the fastening device to a leg section receptacle of the operating table, the connection member including a snap-in mechanism; and
a button configured to snap out of the snap-in mechanism.

8. A fastening device for an operating table, comprising:
a housing having a receptacle that receives a coupler of an operating table device;
a locking bar connected to the housing and movable relative to the housing between a locked position and an unlocked position, the locking bar retaining the coupler in the receptacle in the locked position, and the locking bar releasing the coupler from the receptacle in the unlocked position;
a torsion spring that urges the locking bar toward the locked position;
a lever that moves the locking bar from the locked position to the unlocked position; and
a ratchet assembly that maintains the locking bar in the unlocked position;
wherein the ratchet assembly maintains the locking bar in the unlocked position, when the coupler is disposed in the receptacle and the locking bar has been moved by the lever into the unlocked position, at least until the coupler is removed from the receptacle or the lever is actuated again.

9. The fastening device of claim 1, further comprising:
a feeler member rotatably fastened to the housing, the feeler member urged via a resilient member to a first position in which the feeling member protrudes at least partially into the receptacle;
wherein the feeler member is moved against a resetting force of the resilient member from the receptacle into the housing; and
wherein when the coupler is disposed in the receptacle, the feeler member is moved from the first position to a second position and is maintained by the coupler in the second position as long as the coupler is disposed in the receptacle.

10. The fastening device of claim 9, wherein:
the ratchet assembly includes a first ratchet wheel, a second ratchet wheel, and a square washer, which are mounted in a torque-resistant manner on a shaft;
wherein the ratchet assembly includes a blocking member preloaded in a blocked position, the blocking member engaging with the second ratchet wheel in the blocked position and preventing a rotation of the shaft in a first direction; and
wherein in a released position, the blocking member allows a rotation of the shaft in the first direction.

11. The fastening device of claim 10, wherein:
the feeler member when disposed in the first position contacts the blocking member and holds the blocking member in the released position against the preloading of the blocking member; and
the blocking member is disposed in the blocked position when the feeler member is disposed in the second position.

12. The fastening device of claim 11, wherein:
the locking bar includes a protrusion, the protrusion being engaged with the square washer so that the square washer maintains the locking bar in the unlocked position; and
when the square washer is disposed in a blocking angular position, the blocking member is disposed in the blocked position and the locking bar is moved by the lever to a position past the unlocked position.

13. The fastening device of claim 12, wherein:
in an unblocking angular position, the square washer allows the locking bar to be moved from the unlocked position into the locked position; and
a shape of the first ratchet wheel and a shape of the square washer are adjusted to each other so that when the first ratchet wheel is rotated by a notch, the alignment of the square washer changes between the blocking angular position and the unblocking angular position.

14. The fastening device of claim 10, wherein:
a contact member is disposed on the locking bar, the contact member contacting the first ratchet wheel; and
when the lever is actuated, the contact member rotates the first ratchet wheel by one notch in a direction opposing the first direction.

15. The fastening device of claim 14, wherein the contact member is disposed resiliently relative to the locking bar in a recess of the locking bar such that the contact member it is at least partially movable into the locking bar.

16. An assembly, comprising:
an operating table;
a patient-support device including two rails;
a device-side fastening assembly disposed on each rail; and
a plurality of operating-table-side fastening devices disposed on the operating table, each of the plurality of operating-table-side fastening devices including
a housing having a receptacle that receives a coupler of the device-side fastening assembly;
a locking member connected to the housing and movable relative to the housing between a locked position and an unlocked position, the locking member retaining the coupler in the receptacle in the locked position, and the locking member releasing the coupler from the receptacle in the unlocked position;
a resilient member that urges the locking member toward the locked position;
an actuation member that moves the locking member from the locked position to the unlocked position; and
a ratchet assembly that maintains the locking member in the unlocked position;
wherein the ratchet assembly maintains the locking member in the unlocked position when the coupler is disposed in the receptacle and the locking member has been moved into the unlocked position by a first actuation of the actuation member; and
wherein the ratchet assembly releases the locking member from the unlocked position when either the coupler has been removed from the receptacle or the actuation member is actuated a second time;
wherein each rail is fastened to the operating table via each of the device-side fastening assemblies being attached to a respective one of the plurality of operating-table-side fastening devices.

17. The assembly of claim 16, wherein either
the plurality of operating-table-side fastening devices are not connected directly via a connection member to each other, or
the device-side fastening assemblies are not connected directly via a connection member to each other.

18. The assembly of claim 16, wherein:
each device-side fastening assembly includes a mounting unit fastenable to the device-side fastening assembly and with an intermediate piece fastened rotatably, relative to the mounting unit, about a rotation axis;
the intermediate piece includes the coupler that is disposed into the receptacle;
the intermediate piece includes a plate;
the plate of the intermediate piece includes two recesses disposed on opposite sides at a same distance from the rotation axis;
a plate of the mounting unit includes a recess, which is arranged at the same distance from the rotation axis as the two recesses of the intermediate piece; and
a rotation axis and a longitudinal axis of the coupler do not intersect.

19. The assembly of claim 18, wherein:
the mounting unit includes a bolt receptacle;
the intermediate piece includes a bolt that is rotatably mounted in the bolt receptacle, a longitudinal axis of the bolt forming the rotation axis;
in a first mounting position, the recess of the mounting unit and one of the recesses of the intermediate piece overlap; and
in a second mounting position, the recess of the mounting unit overlaps with the other recess of the intermediate piece.

20. The assembly of claim 19, wherein:
the mounting unit includes a spring bolt that prevents a rotation of the intermediate piece relative to the mounting unit, which is arranged on the side of the plate of the mounting unit facing the plate of the intermediate piece, behind the recess of the mounting unit;
a bolt of the spring bolt is preloaded via a spring of the spring bolt into a secure position in which the bolt extends through the mutually overlapping recesses; and
the bolt is movable against the spring force in a twisted position in which the intermediate piece is rotatable relative to the mounting unit.

\* \* \* \* \*